United States Patent [19]

Burger

[11] Patent Number: 4,815,475
[45] Date of Patent: Mar. 28, 1989

[54] MODULATION SYSTEM FOR EVOKED RESPONSE STIMULATION AND METHOD

[76] Inventor: Howard Burger, 255 North Rd., Chelmsford, Mass. 01824

[21] Appl. No.: 57,220

[22] Filed: Jun. 2, 1987

[51] Int. Cl.$^4$ ............................................. A61B 15/05
[52] U.S. Cl. ..................................... 128/741; 128/783
[58] Field of Search .................. 128/424, 420 A, 421, 128/783, 804, 739, 741

[56] References Cited

U.S. PATENT DOCUMENTS 4,612,934 9/1986 Borkan ................................ 128/421

Primary Examiner—Francis Jaworski
Assistant Examiner—George Manuel
Attorney, Agent, or Firm—Pearson & Pearson

[57] ABSTRACT

A modulation system used for non-surgical biomedical stimulation and for research in the area of evoked responses and a method thereof is described. The modulation system comprises an AND gate used to gate the interaction of a variable frequency oscillator with the inputs from a manual safety and control switch connected to an inverter which is connected to a third input of the AND gate. A second variable frequency oscillator has a non-inverted output Q. The non-inverted output Q is connected to the second input of the AND gate. The second variable frequency oscillator has an on/off duty cycle. The first variable frequency oscillator has an output which has a pulse repetition waveform. The output of the first variable frequency oscillator is connected to the first input of the AND gate. The pulse repetition waveform of the first variable frequency oscillator has a frequency 100 times greater than the range of the non-inverted output Q frequency. The AND gate has an output connected to the input of a pulse width monostable oscillator. The output of the AND gate is a composite of the pulse repetition waveform and the non-inverted output Q which is connected to the input of a stimulation device such as a CW laser. The method of generating evoke responsive stimulation pulses comprises adjusting the first variable frequency oscillator to obtain a pulse waveform then adjusting the second variable frequency oscillator to obtain a second pulse waveform which generate evoked response stimulation pulses. The evoked response stimulation pulses are then applied to a person.

22 Claims, 2 Drawing Sheets

MODULATION SYSTEM FOR EVOKED RESPONSE STIMULATION AND METHOD

FIELD OF THE INVENTION

The present invention relates to an evoked response stimulation system intended for biomedical applications. More particularly, the present invention relates to a modulation system for evoking a response stimulation and a method thereof.

BACKGROUND OF THE INVENTION

Electric stimulation and low-power laser devices principally dominate the field of evoked response stimulation. However, several other devices may be utilized as stimulation sources such as devices using magnetic and electromagnetic fields, non-coherent light, acoustic energy sources, and electrical or mechanical impulses.

A rather limited range of modulation schemes have been used to control the above mentioned devices. Pertinent references include the following: U.S. Pat. No. 3,085,566 to Tolles which describes a measuring device wherein a pair of sinusoidal electrical wave forms may be applied either singly or summed together as phasors such that the patient receives the vector sum of both waveforms. U.S. Pat. No. 3,900,020 to Lock describes an electric acupuncture device which employs two oscillators and is arranged so that each oscillator can be applied to separate needles or probes such that no common ground exists between the outputs of the oscillators. This design permits no interaction between the oscillators. U.S. Pat. No. 4,052,978 to Eugenio describes an electrotherapy apparatus which employs a single low frequency oscillator and detection means to locate and treat diseased organs by the application of electrical currents. U.S. Pat. No. 4,112,923 to Tomocek describes an antonomic transcutaneous affect device which employs a single oscillator and controls for timing, intensity, frequency, and waveform polarity. In addition, a circuit is provided to locate desired acupuncture points. U.S. Pat. No. 4,589,417 to Eseifan describes an apparatus for selective measuring and treating disordered tissues which employs a single oscillator in conjunction with a sensing device to establish and treat specific acupuncture points.

In addition the European market has a device which employs a chain of monostable oscillators to allow independent adjustment of pulse repetition rate, pulse train on time, pulse train off-time, and insertion of intermediate pulses between pulse trains. This device employs a pulse repetition rate modulator control unit which is separate from the CW laser unit and which was originally designed to be used for direct electrical stimulation with the laser interaction as an after thought. The pulse width of this modulator is fixed in the design and not under operator control. Laser output amplitude is, however, manually adjustable.

At the present time, this area of the art includes biostimulation lasers which can be divided into: Continuous Wave (CW) lasers (employing tubes or solid state CW diodes), Pulse Lasers (employing Q switching or solid state pulse diodes). In addition, each of the above two categories can be divided into species by modulation to include: binary scaled pulse repetition rate dividers, analog (music, noise, or tone), and variable on/off modulation.

In general, CW lasers are available with either no modulation or with variable frequency (e.g., on/off) modulation. Pulse diode lasers are virtually all of the binary scaled divider type (usually employing 7 or 8 fixed divide-by-2 scaling options), However, there is no clear-cut line. And, units are available with some of these simple modulation options and with independent CW and Pulse laser sources controlled from a single enclosure.

The purpose of any modulation is to vary the stimulation provided to the subject. Stimulation appears to be a function of the following:

a. The modulation or lack thereof (e.g., a continuous wave) on the incident laser beam or other stimulation source.

b. The wavelength of the laser affects the penetration depth into the skin surface (as well as underlying tissue) and may affect different photosensitive electrolyte compounds differently. It is also suspected that the compressive acoustic wavelength of ultrasonic sources and the electromagnetic wave (e.g., transverse wave, per Maxwells equations) may have some bearing on the overall stimulation of the patient.

c. The location of the incident laser beam or other type of source on the skin surface.

d. The pattern created in the nervous system when multiple laser beams and/or other stimulation sources are used simultaneously on the patient.

e. The power level of the energy beam and the duration that the beam is applied to the subject.

It should be noted that safety (principally eye safety) is a major factor in the use of any laser device. An implicit goal in the development of a laser and modulation system used for biostimulation is to minimize both the peak and the average beam energy required to effect a given type of stimulation. It is clear that most of the devices currently on the market have ignored this factor. As a result, many devices exist which constitute a potential eye hazard if improperly employed. Moreover, a few of the latest devices have sufficient beam energy where damage to skin cells may be concurrent with improper use.

Non-laser, non-electrical stimulation sources are principally of the diathermy (e.g., high frequency electromagnetic waves) and ultrasound (e.g., ultrasonic acoustic wave types). When employed in a pulsed mode both are generally gated at twice the line frequency (e.g., 100 Hertz in Europe and 120 Hertz in North America). Electromagnetic sources, while quite rare, generally appear to employ some form of the aforementioned binary scaled modulation.

SUMMARY OF THE INVENTION

One aspect of the present invention is a novel and improved modulation system for generating evoked response stimulation pulses.

The modulation system comprises, in combination: a first variable frequency oscillator, a second variable frequency oscillator, a first adjustment means, a second adjustment means, a gating means, and a stimulation means.

The first variable frequency oscillator has an output. The output of the first variable frequency oscillator is a first pulsed waveform which has a first pulsed waveform frequency.

The second variable frequency oscillator has an output. The output of the second variable frequency oscillator is a second pulsed waveform which has a second pulsed waveform frequency.

The first pulsed waveform frequency is greater than the second pulsed waveform frequency.

The first adjustment means is for adjusting the first variable frequency oscillator. The first adjustment means is operably connected to the first variable frequency oscillator.

The second adjustment means is for adjusting the second variable frequency oscillator. The second adjustment means is operably connected to the second variable frequency oscillator.

The gating means effectuates a logical operator AND. The gating means has a first input, a second input, and an output. The first input of the gating means is operably connected to the output of the first variable frequency oscillator. The second input of the gating means is operably connected to the output of the second variable frequency oscillator.

The stimulation means evokes a response stimulation from a person. The stimulation means has an input and an output. The input of the stimulation means being operably connected to the output of the gating means. The output of the stimulation mean is the evoked response stimulation pulses.

Another aspect of the present invention is a novel and improved modulation system for generating evoked response stimulation pulses.

The modulation system comprises, in combination: a first variable frequency oscillator, a second variable frequency oscillator, a first adjustment means, a second adjustment means, a ground referencing means, a gating means, a pulse width modulating means, and a stimulation means.

The first variable frequency oscillator has an output. The output of the first variable frequency oscillator is a first pulsed waveform which has a first pulsed waveform frequency. These pulses are usually rectangular.

The second variable frequency oscillator has an output. The output of the second variable frequency oscillator is a second pulsed waveform which has a second pulsed waveform frequency. These pulses are always rectangular.

The first pulsed waveform frequency is greater than the second pulsed waveform frequency.

The first adjustment means is for adjusting the first variable frequency oscillator. The first adjustment means is operably connected to the first variable frequency oscillator.

The second adjustment means is for adjusting the second variable frequency oscillator. The second adjustment means is operably connected to the second variable frequency oscillator.

The ground referencing means has a safety switching means and an inverting means. The safety switching means is operably connected to the inverting means and ground.

The gating means effectuates a logical operator AND. The gating means has a first input, a second input, a third input, and an output. The first input of the gating means is operably connected to the output of the first variable frequency oscillator. The second input of the gating means is operably connected to the output of the second variable frequency oscillator. The third input of the gating means is operably connected to the inverting means.

The pulse width modulating means for controlling pulse width has an input and an output. The input of the pulse width modulating means is operably connected to the output of the gating means.

The stimulation means evokes a response stimulation from a person. The stimulation means has an input and an output. The input of the stimulation means is operably connected to the output of the pulse width modulating means. The output of the stimulation means is the evoked response stimulation pulses.

A further aspect of the present invention is a novel and improved method of generating evoked response stimulation pulses.

The method comprises the following steps:

Step 1—A first adjustment means of a first variable frequency oscillator is adjusted to obtain a first pulsed waveform which has a first pulsed waveform frequency.

Step 2—A second adjustment means of a second variable frequency oscillator is adjusted to obtain a second pulse waveform which has a second pulsed waveform frequency.

Step 3—Evoked response stimulation pulses are applied to a person. The evoked response stimulation pulses are generated from an output of a stimulation means. The stimulation means has an input operably connected to an output of a gating means. The gating means effectuates a logical operator AND. The gating means has a first input and a second input. The first input of the gating means is operably connected to an output of a first variable frequency oscillator. The output of the first variable frequency oscillator is the first pulsed waveform from Step 1. The second input of the gating means is operably connected to an output of a second variable frequency oscillator is the second pulsed waveform from Step 2.

BRIEF DESCRIPTION OF THE DRAWINGS

The various objects, advantages, and novel features will be more fully apparent from a reading of the following detailed description when read in connection with the accompanying drawing, in which like numerals refer to like parts, and in which.

DETAILED DESCRIPTION OF THE PREFERRED EMBODIMENTS

Figure 1:
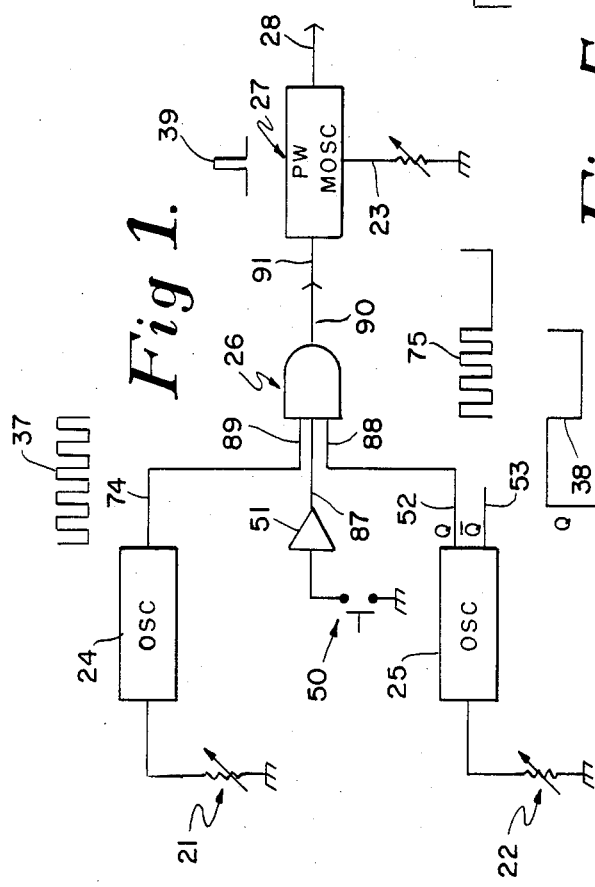
FIG. 1 is a schematic block diagram of diagram of the simplest embodiment of the invention. Also shown is the relationship between the invention and the plurality of transducers potentially to be used with the invention.

This invention deals specifically with a type of modulation which enhances evoked response stimulation pertaining to neurological and biophysical applications. Specifically, it is a hybrid of low frequency on/off modulation with an approximate 50% duty cycle used to gate higher frequency pulse trains. This modulation appears more stimulating than either waveform when separately employed. Both the on/off rate and the rate of high frequency pulse generation may be varied. In addition, the pulse width may also be varied. The ratio of on to off is held essentially constant at a nominal 50% duty cycle.

The techniques disclosed in this invention are intended to minimize the amount of energy and treatment time from any particular energy source employed for experimentation and/or treatment in neurological and/or biophysical stimulation while permitting maximum effectiveness from single or grouped lasers (or other energy sources) in achieving a desired evoked response mechanism.

In addition, a technique is described to allow extension of this modulation to a group of lasers by employing a circuit to effect coordination between their respective modulations. This approach permits a greater range of experimental evoked response strategies to be employed while minimizing the energy employed in any given laser beam or other energy source used to evoke stimulation.

The means used to generate the basic modulation timing may be simple variable frequency oscillators of common form. These may also be replaced by sophisticated digitally based frequency synthesizers of the type commonly found in radios. The important feature appears to be the ability to allow for fine (preferably continuous) incrementation. The subject who is being stimulated appears to vary much more than the stability of even the crudest variable frequency oscillator.

Control of the system may be manual where the operator adjusts the oscillators and controls the application time. More sophisticated implementations are also possible where an evoked response sensing device is monitored by a microprocessor based system which alters control settings and application interval based upon evoked biophysical or neurological indicators. Pulse width may be similarly made variable.

The actual wavelength used for stimulation is determined by the stimulation source employed. Given the current state of the art, it is assumed that:

a. The wavelength of lasers is fixed by design. Although it is acknowledged that variable wavelength lasers exist in laboratories, these lasers are too expensive and cumbersome to consider for this application at the present time.

b. Ultrasonic acoustic devices are generally resonant at a single frequency with little or no provision to vary the wavelength of the acoustic emission other than changing the emitter itself to one cut for a different frequency.

c. Diathermy and low/high frequency electromagnetic sources may be designed with fairly substantial tuning ranges.

d. Direct contact transcutaneous electrical stimulation may be designed with fairly broad wavelength tuning ranges, if so desired.

e. Electromechanical devices (e.g., Solenoidal or similar linear motion transducers) may also operate over a fairly broad tuning range, if so desired.

It should be clear that while tuning of the emitted wavelength is quite possible for many types of stimulation sources, the most basic embodiments of this modulation technique will not employ this feature owing to operational complexity and cost constraints.

Figure 2:
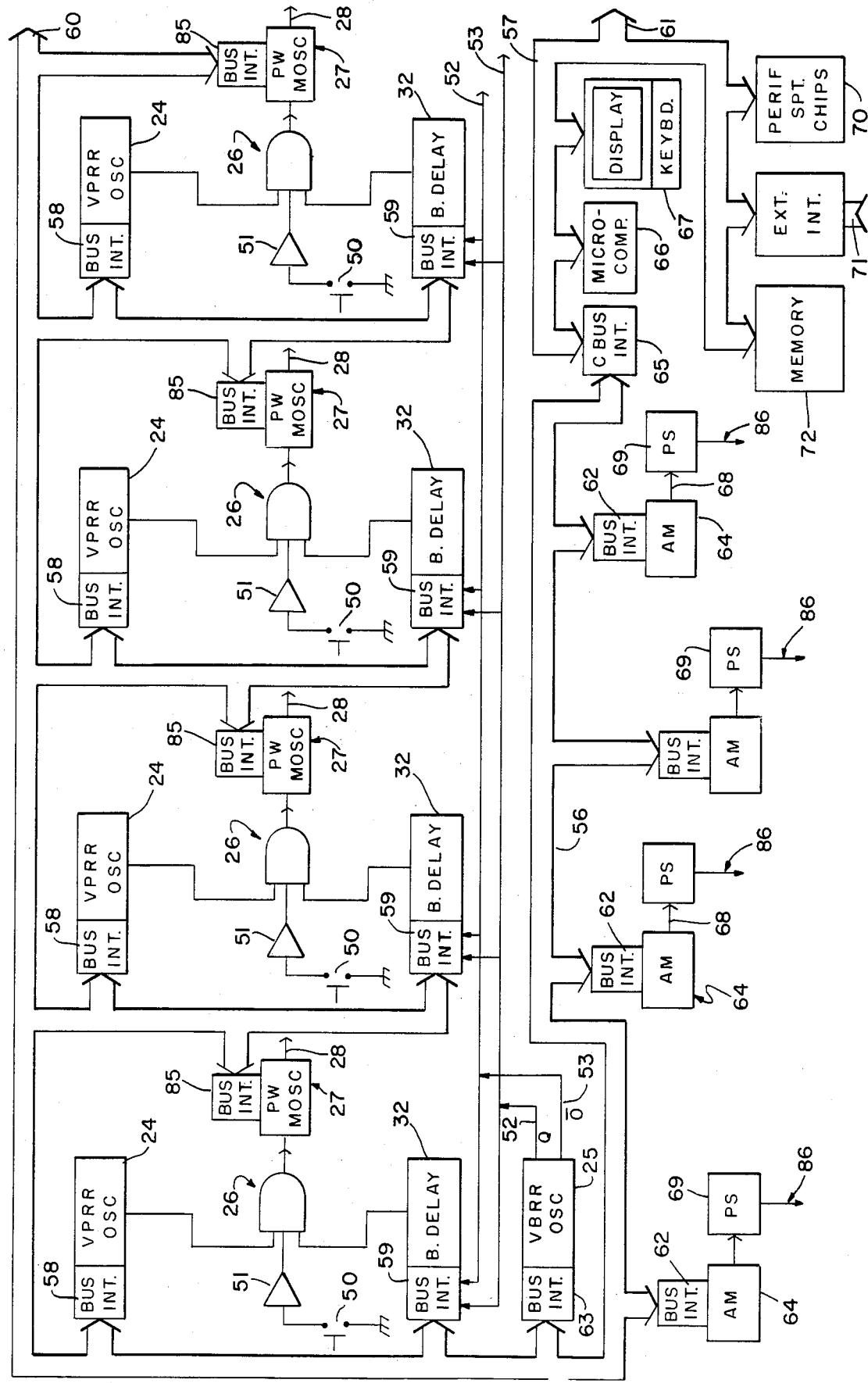
FIG. 2 is a schematic block diagram of how this invention may be setup to allow for microprocessor control over each stimulation source and how an external sensor may be interfaced and used to alter control settings in place of a human operator. In this embodiment signal amplitude as well as pulse repetition rate is accomplished within the physical limits of each transducer.

FIGS. 1 and 2 each employ similar numbers to indicate similar elements. FIG. 1 depicts a preferred embodiment of the present invention. The modulation system for evoked response stimulation is shown in FIG. 1 comprises gating means 26, such as a (N)AND gate, for effecting a logical operator AND. Gating means 26 is used to gate the interaction of first variable frequency oscillator 24, such as a Signetics SE566 function generator with the inputs from: (a) manual safety and control switch 50, such as a single pole single throw momentary contact normally open switch, which is shown in FIG. 1 operably connected to inverter 51 which is operably connected to third input 87 of gating means 26. Manual safety and control switch 50 maintains the convention of using the ground as a reference. (b) Second variable frequency oscillator 25 has an output 52 which has a second pulsed waveform 38, such as a non-inverted output Q. Second pulsed waveform 38 has a second pulsed waveform frequency. Output 52 of second variable frequency oscillator 25 is operably connected to second input 88 of gating means 26. Second variable frequency oscillator 25 has an on/off duty cycle. The preferred duty cycle is from about 50 percent on and 50 percent off. Lesser preferred duty cycle range is from about 30 percent on and 70 percent off to about 70 percent on and 30 percent off. Normal build tolerances might have a variation of 20 percent in duty cycle. (c) First variable frequency oscillator 24 has an output 74 which has a first pulsed waveform 37, such as a pulse repetition waveform. Output 74 is operably connected to a first input 89 of a gating means 26. First pulsed waveform 37 has a first pulsed waveform frequency which has a range of about 100 times greater than the range of the second pulse waveform frequency of second pulse waveform 38. The range of the first pulsed waveform frequency is from about 50 to 2,000 Hertz.

Gating means 26 has an output 90 operably connected to input 91 of pulse width modulating means 27, such as a pulse width monostable oscillator, or alternatively output 90 can be operably connected directly to input 30 of the stimulation means. Gating means 26 may also be controlled in response to an output from an evoked response sensing means as received by an interfacing means and computed by a processor means. Output 90 of gating means 26 has a composite waveform 75 which is a composite of first pulsed waveform 37 and second pulsed waveform 38. As shown in FIG. 1, waveform 75 is further conditioned by pulse width modulating means 27 generating a final waveform 40 at output 28 of pulse width modulating means 27. Pulse width modulating means 27 has a pulse width waveform 39. The final width of final waveform 40 is established either by an operator who varies and controls pulse width modulating means by employing control input 23, such as a variable resistor, or, as shown in FIG. 2, by an evoked response sensing means which can vary and control pulse width modulating means 27.

In a similar manner first adjustment means 21, such as a variable resistor, and second adjustment means 22, such as a variable resistor, are employed by an operator to adjust first variable frequency oscillator 24 and second variable frequency oscillator 25 respectively, or, as shown in FIG. 2, a signal generated in an evoked response sensing means can be used to alter the first pulsed waveform frequency of first variable frequency oscillator 24 or the second pulsed waveform frequency of second variable frequency oscillator 25. First adjustment means 21 is operably connected to first variable frequency oscillator 24 and second adjustment means 22 is operably connected to second frequency oscillator 25 as shown in FIG. 1.

Final waveform 40 or alternatively composite waveform 75 establishes the final pulse width received by input 30 of the stimulation means. The stimulation means comprises stimulation devices such as: CW laser 29, CW or Q-switched laser 83, laser 96, piezo electric transducer 81, electromagnetic field transducer 95, a solenoid or a vibratory mechanical device 84, and electric pulse stimulator 97. CW laser 29 has a laser power supply 31 and a CW laser light emission 36. CW or Q-switched laser 83 has a laser power supply 78 without modulation input, a shutter interface 82 for Q-switch or electro optical shutter 93, and a CW or Q-switched laser light emission 92. Pulse laser 96 has a power supply 33, an SCR 34 used as a gating device for pulse laser diode 76, pulse laser diode 76, a charge storage capacitor 35, and a pulse laser light emission 94. Pulse laser 96 relies upon the series resistance of its associate elements (shown in FIG. 1 for simplicity as SCR 34 used as a gating device for pulse laser diode 76 and charge storage capacitor 35) rather than on the final pulse width to limit the rate of current flow 73. In an analagous fashion the electro optical shutter (or Q-switch) 93 would limit pulse width due to physical properties of these devices. Piezo electric transducer 81, such as an acoustic wave transducer, has a power supply 41, and an acoustic wave emission 45. Electromagnetic field transducer 95 has an antenna or coil 80, a power supply 42, and a transverse electromagnetic field emission 46. Linear motion transducer 84 has a power supply 43, a linear pulsating mechanical member 100, a spring 101 and a pulsating mechanical emission 47. And electrical pulse stimulator 97 has an electrical impulse amplifier 77, a power supply 44, a variable resistor 49 for amplitude control over direct stimulation waveform, an output isolation transformer 79, and a direct electrical stimulation output 48 such as a small pulsating electrical voltage Vo.

In each of the devices represented by the final waveform 40 from output 28 or alternatively composite waveform 75 from output 90 received by input 30 of the stimulation means must be designed to accept control inputs from output 28 or alternatively output 90. Also, power supplies must be designed to provide the desired stimulus to the respective stimulation means. The output of each power supply may be AC, DC, and/or RF as required. In general, power supplies are old in the art. What is important is the ability for the transducer of the stimulation means and power supply to provide an appropriate interface at input 30 and transmit appropriate power to the respective transducer.

There is no theoretical limit to the number of stimulation means that can be operably connected to the Q or Q-not outputs of the second variable frequency oscillator 25 other than the fanout of output 28 or 90 respectively. In practice the user would probably be limited by adjustment complexity if the number of stimulation means were greater than four.

It should be noted that second variable frequency oscillator 25 has a Q-not output 53 as shown in FIG. 1. The waveform 54 of Q-not output 53 is the opposite of second pulsed waveform 38. Q-not output 53 can be used to trigger a second AND gate of the same form as gating means 26, thus allowing for alternative blinking, off and on, and controlling of two or more stimulation means such that while first variable frequency oscillator 24 is gated off a third variable frequency oscillator, identical in form to first variable frequency oscillator 24, is gated on.

Conversely, up to the fanout limit of pulse width modulating means 27, any number of stimulation sources may be synchronized off of second variable frequency oscillator 25.

Alternatively, second variable frequency oscillator 25 can be used to drive a counter having counter outputs in which only a single counter output is enabled at any instant. The counter outputs are used to sequentially gate a plurality of additional variable frequency oscillators identical in form to first variable frequency oscillator 24. The identical variable frequency oscillators would each be operably connected to a separate stimulation means such that sequential blinking, on and off, of the separate stimulation means is obtained.

In addition, second variable frequency oscillator 25 can gate first variable frequency oscillator 24 by turning on and off the power supplied to first variable frequency oscillator 24 turning and off the output of first variable frequency oscillator 24.

The evoked response stimulation pulses can have their width determined from the following: a capacitor, an energy discharge circuit means, a transistor gating circuit means, a power supply voltage amplitude means, and a monostable pulse width modulator circuit means, or their width can be determined by an electro-optical shutter means or a Q-switching means.

First variable frequency oscillator 24 and second variable frequency oscillator 25 can be replaced by frequency synthesizers having a resolution equal to or less than 1/10.

FIG. 2 depicts a substantially more complicated embodiment of the present invention which utilizes a micro processor 66, such as a micro computer, to effect control and coordination among the many elements.

This embodiment includes both a stimulation control bus 56, a micro computer interface bus 57 to effect both control over the other elements, and an external interface port 71 to allow the use of external sensor means. The signals received through external interface port 71 are evaluated by micro processor 66 and using commands stored in micro computer memory 72 outputs commands through control bus interface 65.

The user is interfaced to the system via the display/keyboard unit 67 thus providing access to all aforementioned elements plus periferal support chips 70.

The elements in FIG. 1 have been modified to allow automation and near real time control in FIG. 2. The modifications are: First variable frequency oscillator 24, shown in FIG. 2, now connects through stimulation bus interface 58. Second variable frequency oscillator 25, shown in FIG. 2, now connects through stimulation bus interface 63, and pulse width modulating means 27, shown in FIG. 2, now connects through stimulation bus interface 85.

Amplitude modulator (AM) control 64 acting via bus interface 68 through power supply means 69, such as power supplies 31, 33, 41, 42, 43, 44, and 78 which permits the amplitude control of each stimulation means connected to transducer output 86 to be varied in near real time as determined by micro processor 66. The stimulation control bus 56 supplies data to amplitude modulator means 64 using bus interface 62. Bus interface 60 interfaces with extended stimulation control bus 56 and bus interface 65 interfaces with micro computer bus 57. The stimulation bus 56 interfaces with variable blink delay oscillator 32 at bus interface 59.

Even though a micro processor is performing the major control functions, manual safety and control switch 50 is still retained for reasons of safety on each gating means 26 shown in FIG. 2.

SELECTION OF OPERATING PARAMETERS

The modulation parameters are bounded by the physical limitations of the stimulation sources employed. It is also bounded by associated circuit components. In practice, however, the modulation required to achieve normal stimulation is easily within the boundaries of current circuit technology. The ratio of the maximum blink frequency to the maximum pulse repetition rate is about 1 to 100.

By experimentation it has been found that by adjusting the pulse repetition rate, a point of maximum sensation can be found. This adjustment point varies from person to person and also apparently with the health of the area being stimulated. Below and above the adjustment for maximum sensation nothing is felt during short periods of stimulation. Often, when a laser is adjusted to the setting for maximum sensation, the subject often perceives stimulation a substantial distance away from the point on the body at which the laser is aimed. This sensation is generally repeatable from individual to individual. Although, it should be noted that certain individuals claim to feel nothing regardless of laser setting or duration of exposure.

This maximum point setting that a particular individual feels appears, on the average to be constant over a long period of time. It appears to drop under the following conditions:

a. A general illness such as cold or flu will cause a measurable drop of the maximum stimulation frequency. If the illness is very severe the feeling of stimulation may be entirely absent.

b. A bruise or other physical injury will produce a localized drop in the maximum stimulation frequency. The frequency will increase as healing occurs and the bruise goes away. Concurrently, the laser appears to speed up the time it takes for bruises to disappear. The maximum stimulation frequency will remain below normal for several days after the visible effects of an injury have disappeared.

Large scale statistical trials have not been undertaken, however, the median maximum stimulation frequencies appear to be about 200 pulses per second for men with women running up to several times this rate. Based upon the foregoing, a maximum stimulation frequency of 2000 pulses per second was chosen as a practical limit for experimentation. Although, certain equipments have been built with pulse repetition rates up to 399,999 pulses per second.

Below and above the setting for maximum stimulation some local stimulation can often be felt after very long periods compared to those required at the setting for maximum stimulation. These other settings are not without experimental interest. However, fairly sophisticated evoked response sensing equipment is required to analyze the results achieved from the use of these settings.

In the course of experimenting with different pulse repetition rates it became apparent that some mechanism was desirable to speed up the evoked response stimulation process. The prevailing European approach has been to go to higher and higher power levels with general disregard for the safety implications this raises. European literature does not generally draw a distinct line between a laser for evoked response stimulation and using it for concurrent tissue heating.

The incorporation of a dual modulation technique was tried to speed up the achievement of an evoked response while minimizing the average power level required to achieve a desired response. This dual modulation consists of the above described pulse repetition rate adjustment approach coupled with a secondary modulation rate that gates the primary (and higher) modulation rate on and off. For convenience this is referred to as "blinking".

The blink frequency range was chosen by experimentation. Within the upper pulse repetition rate bound chosen at 2000 pps, a blink rate of 8-10 hertz appears to enhance the effectiveness of the basic pulsed waveform. This correlates nicely with the electrical stimulation theory developed by Voll over the last 40 years or so. While more sophisticated evoked response monitors may extend this range, an upper bound of 20 hertz was chosen based upon the limits of utility perceivable without sophisticated instrumentation. The 50% duty cycle was also chosen by similar experimentation.

While these values appear very effective, further refinement may be possible with more sophisticated instrumentation than is currently available. As such, the upper and lower boundaries for both the pulse repetition rate and the blink rate may shift somewhat as may the blink duty cycle limits.

It is possible to extend the basic modulation concept to incorporate stimulation energy patterns generated on different parts of the subject through the coordinated use of multiple energy sources.

The choice of the patterns to be generated by a system of this kind is based upon the perceived need to stimulate multiple points in precisely defined ways in order to evoke different neurological/biophysical responses and/or to enhance the response achieved by stimulating a single point.

While there has been shown and described what is at present considered the preferred embodiment of the invention, it will be obvious to those skilled in the art that various changes and modifications may be made therein without department from the scope of the invention.

I claim:

1. A modulation system for generating evoked response stimulation pulses comprising:

a first variable frequency oscillator having an output, said output of said first variable frequency oscillator being a first pulsed waveform, said first pulsed waveform having a first pulsed waveform frequency, said first pulsed waveform frequency having a range of frequencies;

a second variable frequency oscillator having an output, said output of said second variable frequency oscillator being a second pulsed waveform, said second pulsed waveform having a second waveform frequency, said second pulsed waveform frequency having a range of frequencies;

said first pulsed waveform frequency range being greater than said second pulsed waveform frequency range;

a first adjustment means for adjusting said first variable frequency oscillator, said first adjustment means being connected to said first variable frequency oscillator;

a second adjustment means for adjusting said second variable frequency oscillator, said second adjustment means being connected to said second variable frequency oscillator;

a gating means for effecting a logical operator AND, said gating means having a first input, a second input, and an output, said first input of said gating means being connected to said output of said first variable frequency oscillator, said second input of said gating means being connected to said output of said variable frequency oscillator; and a stimulation means for evoking a response stimulation from a person, said stimulation means having an input and an output, said input of said stimulation means being connected to said output of said gating means; said output of said stimulation means being evoked response stimulation pulses, said stimulation means comprising a stimulation source selected from the group consisting of a laser, a piezoelectric transducer, an electric pulse stimulator, an electromagnetic field transducer, a linear motion transducer, non-coherent light pulsed magnetic field generator and combinations thereof.

2. A modulation system in accordance with claim 1 wherein said first pulsed waveform frequency has a range about 100 times greater than the range of said second pulsed waveform frequency.

3. A modulation system in accordance with claim 1 wherein said first pulsed waveform frequency has a range from about 50 to 2,000 Hertz and second pulsed waveform frequency comprises a range from about 0.1 to about 20 Hertz.

4. A modulation system in accordance with claim 1 wherein said second variable frequency oscillator maintains a duty cycle for said first variable frequency oscillator by alternating said first pulsed waveform from said output of said gating means, said duty cycle being an on/off duty cycle.

5. A modulation system in accordance with claim 4 wherein said duty cycle compresses a range from about 10 percent on and 90 percent off to about 90 percent on and 10 percent off.

6. A modulation system in accordance with claim 4 wherein said duty cycle comprises a range from about 30 percent on and 70 percent off to about 70 percent on and 30 percent off.

7. A modulation system in accordance with claim 5 wherein said duty cycle comprises about 50 percent on and 50 percent off within a plus or minus 20 percent variation.

8. A modulation system in accordance with claim 1 wherein said second variable frequency oscillator is provided with Q and Q-not outputs such that while said first variable frequency oscillator is gated on a third variable frequency oscillator, identical in form and function to said first variable frequency oscillator is gated off, thus allowing a pair of stimulation means to be alternately blinked on and off, said third variable frequency oscillator being connected to second gating means, said Q-not output of said second variable frequency oscillator being connected to said second gating means, said second gating means being connected to a second stimulation means of said pair of stimulation means.

9. A modulation system in accordance with claim 8 wherein said Q and Q-not outputs are each used to gate a plurality of variable frequency oscillators, identical in form and function to said first variable frequency oscillator, each of which is thence connected to separate stimulation means such that all said separate stimulation means related to said Q output are blinked on at the same time and separate stimulation means related to said Q-not output are blinked off, said plurality of variable frequency oscillators being connected to corresponding gating means, said corresponding gating means being connected to corresponding said separate stimulation means.

10. A modulation system in accordance with claim 1 wherein said second variable frequency oscillator is used to drive a counter having counter outputs in which only a single counter output is enabled at any instant, said counter outputs being used to sequentially gate a plurality of additional variable frequency oscillators, identical in form and function to said first variable frequency oscillator; and said identical variable frequency oscillators each operably connected to a separate stimulation means for sequential blinking of said separate stimulation means, said counter outputs being connected to said plurality of additional variable frequency oscillators.

11. A modulation system in accordance with claim 10 wherein said counter outputs are each used to gate a plurality of variable frequency oscillators, identical in form and function to said first variable frequency oscillator, each of which is thence connected to separate stimulation means such that all said separate stimulation means connected to each separate said counter outputs are blinked on at the same time all other said separate stimulation means are blinked off.

12. A modulation system in accordance with claim 1 wherein said evoked response stimulation pulses have a width, said width being variable and controlled by an operator or an evoked response sensing means.

13. A modulation system in accordance with claim 1 wherein said gating means may additionally be controlled in response to an output from an evoked response sensing means received by an interfacing means and computed by a processor means.

14. A modulation system in accordance with claim 1 wherein said first pulsed waveform frequency is altered as a result of a signal generated in an evoked response sensing means.

15. A modulation system m in accordance with claim 1 wherein said second pulsed waveform frequency is altered as a result of a signal generated in an evoked response sensing means.

16. A modulation system in accordance with claim 1 wherein said second variable frequency oscillator gates said first variable frequency oscillator by turning on and off power supplied to said first variable frequency oscillator said power being connected to said variable frequency oscillator.

17. A modulation system in accordance with claim 1 wherein said second variable frequency oscillator gates said first variable frequency oscillator by turning on and off said output of said first variable frequency oscillator, said output of said first variable frequency oscillator being connected to second variable frequency oscillator.

18. A modulation system in accordance with claim 1 wherein said evoked response stimulation pulses have a width which is determined from a means selected from the group consisting of a capacitor energy discharge circuit means, a transistor gating circuit means, a power supply voltage amplitude means, a monostable pulse width modulator circuit means, and combinations thereof.

19. A modulation system in accordance with claim 1 wherein said evoke response stimulation pulses have a width which is determined by a means selected from the group consisting of an electro-optical shutter means, a Q switching means, and combinations thereof.

20. A modulation system in accordance with claim 1 wherein said first variable frequency oscillator and said second variable frequency oscillator are replaced by frequency synthesizers having a resolution equal or less than 1/10 of an octave.

21. A modulation system for generating evoked response stimulation pulses comprising:

a first variable frequency oscillator having an output, said output of said first variable frequency oscillator being a first pulsed waveform, said first pulse waveform having a first pulsed waveform frequency;

a second variable frequency oscillator having an output, said output of said second variable frequency oscillator being a second pulsed waveform, said second pulsed waveform having a second pulsed waveform frequency;

said first pulsed waveform frequency being greater than said second pulsed waveform frequency;

a first adjustment means for adjusting said first variable frequency oscillator, said first adjustment means being connected to said second variable frequency oscillator;

a ground referencing means having a safety switching means and an inverting means, said safety switching means being connected to said inverting means, and ground, said ground referencing means being connected to ground and said gating means;

a gating means for effecting a logical operator AND, said gating means having a first input, a second input a third input, and an output, said first input of said gating means being connected to said output of said first variable frequency oscillator, said second input of said gating means being connected to said output of said second variable frequency oscillator, said third input of said gating means being connected to said inverting means;

a pulse width modulating means for controlling pulse width having an input and an output, said input of said pulse width modulating means being connected to said output of said gating means; and a stimulation means for evoking a response stimulation from a person, said stimulation means having an input and an output, said input of said stimulation means being connected to said output of said pulse width modulating means, said stimulation means comprising a stimulation source selected from the group consisting of a laser, a piezoelectric transducer, an electric pulse stimulator, an electromagnetic field transducer, a linear motion transducer, and combinations thereof.

22. A method of generating evoked response stimulation pulses comprising the following steps:

Step 1—adjusting a first adjustment means of a first variable frequency oscillator to obtain a first pulsed waveform having a first pulsed waveform frequency;

Step 2—Adjusting a second adjustment means of a second variable frequency oscillator to obtain a second pulsed waveform having a second pulsed waveform frequency;

Step 3—applying evoked response stimulation pulses to a person, said evoked response stimulation pulses being generated from an output of a stimulation means, said stimulation means having an input connected to an output of a gating means, said gating means effecting a logical operator AND, said gating means having a first input and a second input, said first input of said gating means being connected to an output of a first variable frequency oscillator, said output of said first variable frequency oscillator being said first pulsed waveform from Step 1, said second input of said gating means being connected to an output of a second variable frequency oscillator, said output of said second variable frequency oscillator being said second pulsed waveform from Step 2, said stimulation means comprising a stimulation source selected from the group consisting of a laser, a piezoelectric transducer, an electric pulse stimulator, an electromagnetic field transducer, a linear motion transducer, and combinations thereof.

* * * * *